US011690533B2

(12) United States Patent
Nakamura et al.

(10) Patent No.: US 11,690,533 B2
(45) Date of Patent: Jul. 4, 2023

(54) HEALTH MANAGEMENT APPARATUS, HEALTH MANAGEMENT METHOD, AND HEALTH MANAGEMENT PROGRAM (71) Applicants: OMRON HEALTHCARE CO., LTD., Muko (JP); OMRON CORPORATION, Kyoto (JP)

(72) Inventors: Fumihiko Nakamura, Kyoto (JP); Daisuke Nozaki, Kyoto (JP); Yasushi Matsuoka, Kyoto (JP)

(73) Assignees: OMRON HEALTHCARE CO., LTD., Muko (JP); OMRON CORPORATION, Kyoto (JP)

(*) Notice: Subject to any disclaimer, the term of this patent is extended or adjusted under 35 U.S.C. 154(b) by 762 days.

(21) Appl. No.: 16/690,628

(22) Filed: Nov. 21, 2019

(65) Prior Publication Data
US 2020/0085346 A1 Mar. 19, 2020

Related U.S. Application Data (63) Continuation of application No. PCT/JP2018/022219, filed on Jun. 11, 2018.

(30) Foreign Application Priority Data

Jun. 19, 2017 (JP) ................................. 2017-119989

(51) Int. Cl.
*A61B 5/11* (2006.01)
*A61B 5/02* (2006.01)
(Continued)

(52) U.S. Cl.
CPC .............. *A61B 5/1118* (2013.01); *A61B 5/02* (2013.01); *A61B 5/4872* (2013.01);
(Continued)

(58) Field of Classification Search
CPC ......... A61B 5/118; A61B 5/02; A61B 5/4872; A63B 24/0021; A63F 3/00697
(Continued)

(56) References Cited

U.S. PATENT DOCUMENTS

2004/0186772 A1 9/2004 Kawatahara

FOREIGN PATENT DOCUMENTS

| CN | 1518717 A | 8/2004 |
| JP | H10-85454 A | 4/1998 |

(Continued)

OTHER PUBLICATIONS

Jul. 20, 2021 Office Action issued in Japanese Patent Application No. 2017-119989.
(Continued)

*Primary Examiner* — Kesha Frisby
(74) *Attorney, Agent, or Firm* — Oliff PLC (57) ABSTRACT

A health management apparatus includes a processor that is configured to activate a sugoroku including squares linking a starting square with a finishing square and direct a piece of a user to be advanced through the squares. The processor is configured to obtain measurement data including biological information of the user and a time of day or location of measurement at which the biological information has been measured. The processor is configured to assess an evaluation value based on whether the time of day or location of measurement satisfies a condition, and determine a number of squares through which the piece is to be advanced in the sugoroku, based on the evaluation value.

10 Claims, 6 Drawing Sheets

(51) Int. Cl.
*A61B 5/00* (2006.01)
*A63B 24/00* (2006.01)
*A63F 3/00* (2006.01)

(52) U.S. Cl.
CPC ...... *A63B 24/0021* (2013.01); *A63F 3/00697* (2013.01); *A63B 2024/0025* (2013.01); *A63F 2003/00779* (2013.01)

(58) Field of Classification Search
USPC ........................................................ 600/301
See application file for complete search history.

(56) References Cited

FOREIGN PATENT DOCUMENTS

| | | | |
|---|---|---|---|
| JP | 2004-258792 | A | 9/2004 |
| JP | 2007-122182 | A | 5/2007 |
| JP | 2010-046347 | A | 3/2010 |
| JP | 2012-161470 | A | 8/2012 |
| WO | 00/074572 | A1 | 12/2000 |

OTHER PUBLICATIONS

Sep. 4, 2018 International Search Report issued in International Patent Application No. PCT/JP2018/022219.
Jan. 28, 2023 Office Action issued in Chinese Patent Application No. 2018800408267.

| Health state | Condition |
|---|---|
| Cerebral infarction or myocardial infarction | Blood pressure measured in morning? |
| SAS | Blood pressure measured at night? |
| Workplace hypertension | Blood pressure measured at workplace? |
| On diet | Body weight measured within specified period of time? |

HEALTH MANAGEMENT APPARATUS, HEALTH MANAGEMENT METHOD, AND HEALTH MANAGEMENT PROGRAM

CROSS-REFERENCE TO RELATED APPLICATIONS

This application is a Continuation Application of PCT Application No. PCT/JP2018/022219, filed Jun. 11, 2018 and based upon and claiming the benefit of priority from Japanese Patent Application No. 2017-119989, filed Jun. 19, 2017, the entire contents of all of which are incorporated herein by reference.

FIELD

The present invention relates to a health management apparatus, a health management method, and a health management program.

BACKGROUND

For the purpose of health management, a subject (user) needs to measure biological information. However, some users are apt to forget to measure biological information. To address this, Jpn. Pat. Appln. KOKAI Publication No. 2004-258792 proposes a prize-based biological measurement system. The prize-based biological measurement system in Jpn. Pat. Appln. KOKAI Publication No. 2004-258792 obtains results of measurements performed by a user and generates a lottery number for a prize based on the results of measurements. According to the prize biological measurement system, the user's motivation to measure biological information can be enhanced. Moreover, according to the above-mentioned prize-based biological measurement system, it is possible to enhance the user's health and prevent the possibility of forgetting to take measurements by requiring the users to transmit measurement results every day as a qualification for entering the prize draw.

SUMMARY

A health management apparatus according to one aspect of the present invention includes: an activation section that activates a sugoroku including a plurality of squares linking a starting square with a finishing Square, and configured to direct a piece of a user to be advanced through the squares from the starting square toward the finishing square; an obtaining section that obtains measurement data on biological information of the user; an assessment section that assesses an evaluation value based on the obtained measurement data; a determination section that determines a number of squares through which the piece is to be advanced in the sugoroku, based on the assessed evaluation value; and an update section that updates location information indicating a square at which the piece is located, based on the determined number of squares.

According to the above-described configuration, the measurement data on the user's biological information is obtained, and the user's piece is advanced in the sugoroku, based on the obtained data. This enhances the user's motivation to measure biological information.

When the piece is advanced in the sugoroku, the location information of the piece is updated and stored. Upon obtaining the next item of measurement data, the location information is further updated and stored. That is, the measurement data obtained from time to time is continuously used in the sugoroku. Thereby, even when the user forgets to make a measurement once (e.g., one day), it is possible to maintain the user's motivation for the subsequent measurements.

Also, an evaluation value, namely, a level of importance is assessed based on the measurement data. Based on the assessed evaluation value, the number of squares through which the piece is to be advanced in the sugoroku is determined. This facilitates a heightening of the user's motivation to measure biological information with a high level of importance.

The health management apparatus according to the above-described one aspect further comprise an awarding section that awards a point to the user when the square indicated by the location information has become the finishing square. According to the configuration, a point is awarded when the piece has been advanced to the finishing square (goal), thereby maintaining the user's motivation to take measurements until the piece reaches the goal.

In the health management according to the above-described one aspect, the assessment section obtains health information indicating a health state of the user, and assesses the evaluation value based on the obtained measurement data and the health information. According to the configuration, an evaluation value is assessed based not only on the measurement data, but also on the user's health information. It is thereby possible to obtain measurement data with a high level of importance specific to the user, thus improving the quality of health management.

In the health management according to the above-described one aspect, the assessment section assesses the evaluation value as a first value when the obtained measurement data does not satisfy a predetermined condition that is based on the obtained health information, and assesses the evaluation value as a second value higher in evaluation than the first value when the obtained measurement data satisfies the predetermined condition that is based on the obtained health information. According to the configuration, it is possible to assess the level of the evaluation value, based on whether or not the measurement data satisfies a predetermined condition based on the user's health information.

In the health management according to the above-described one aspect, the determination section determines the number of squares through which the piece is to be advanced as a first number when the evaluation value is determined as the first value, and determines the number of squares through which the piece is to be advanced as a second number greater than the first number when the evaluation value is determined as the second value. According to the configuration, if the evaluation value is high, the number of squares through which the piece is to be advanced can be large.

In the health management according to the above-described one aspect, the measurement data includes a blood pressure and a time of day of measurement. According to the configuration, the evaluation value can be assessed based on the blood pressure and the time of day of measurement used as the measurement data.

In the health management according to the above-described one aspect, the measurement data includes a blood pressure and a location of measurement. According to the configuration, the evaluation value can be assessed based on the blood pressure and the location of measurement used as the measurement data.

In the health management according to the above-described one aspect, the measurement data includes a body weight and a time of day of measurement. According to the

DETAILED DESCRIPTION

By holding a prize draw based on the results of measurement of biological information as in the system described in Jpn. Pat. Appln. KOKAI Publication No. 2004-258792, the user's motivation to measure such biological information can be enhanced. In addition, by setting daily measurement as a qualification for entering the prize draw, it is possible to enhance the user's health and prevent the possibility of forgetting to take measurements.

However, depending on the user's convenience, it may be difficult to perform daily measurements. In the system described in Jpn. Pat, Appln. KOKAI Publication No. 2004-258792, if a user forgets to perform a measurement once (one day), the user will be disqualified from entering the prize draw. This reduces the user's motivation for performing the subsequent measurements.

Embodiments have been made in view of the above-described circumstances, and aims to provide a technique for enhancing and maintaining the user's motivation to measure biological information.

Hereinafter, an embodiment according to an aspect of the present invention (also referred to as "present embodiment" hereinafter) will be described, with reference to the drawings. In every respect, the present embodiment that will be described below is merely an illustration of the present invention. As a matter of course, various alternations and modifications can be made, without departing from the gist of the invention. That is, in implementing the present invention, a specific configuration may be suitably adopted according to the embodiment. The data appearing in the present embodiment is described with natural language; however, in actuality, it is represented by pseudo language, a command, a parameter, machine language, etc. that can be recognized by a computer.

§ 1 Application Example

Figure 1:
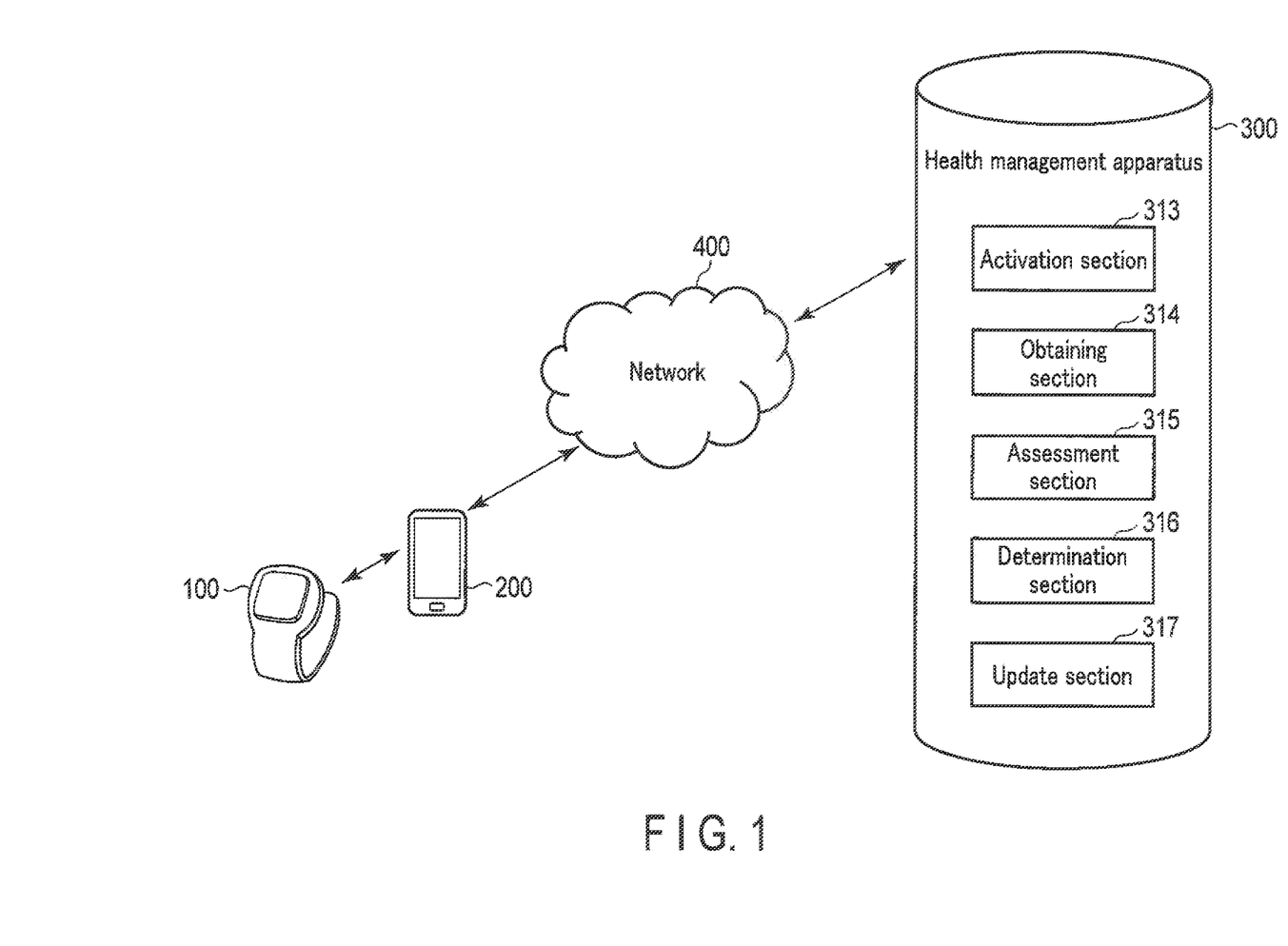
FIG. 1 schematically illustrates an example of a scene in which a health management system according to the embodiment is applied.

First, an example of a scene to which the present invention is applied will be described, with reference to FIG. 1. FIG. 1 schematically illustrates an example of a scene to which a health management system according to the embodiment is applied.

As shown in FIG. 1, the health management system includes a measurement terminal 100, a user terminal 200, and a health management apparatus 300.

In the health management system shown in FIG. 1, the measurement terminal 100 is, for example, wirelessly connected to the user terminal 200. The user terminal 200 and the health management apparatus 300 are connected to each other via a wide-area network 400. The configuration of the health management system is not limited to the configuration shown in FIG. 1.

The measurement terminal 100 may be, for example, connected to the health management apparatus 300 without involvement of the user terminal 200. Part of the functions (processes) realized by the health management apparatus 300 may be executed by the user terminal 200.

The measurement terminal 100 is, for example, a wristwatch-type wearable device. The measurement terminal. 100 is worn by the user to measure biological information such as the user's blood pressure. The measurement terminal 100 generates measurement data containing the measured biological information and information on the time of day of measurement, the location of measurement, etc.

In addition to the measurement terminal 100 (first measurement terminal), an unillustrated measurement terminal (second measurement terminal) may be provided. The second measurement terminal measures, for example, biological information such as the user's body weight. The second measurement terminal generates measurement data containing the measured biological information, and information on the time of day of measurement, the location of measurement, etc. The second measurement terminal is, for example, wirelessly connected to the user terminal 200. Multiple unillustrated measurement terminals may be further provided so as to be, for example, wirelessly connected to the user terminal 200.

The user terminal 200 is, for example, an information communication terminal used by an individual user, and is a portable information communication terminal such as a smartphone, a mobile phone, a tablet PC, a notebook PC, etc. The user terminal 200 transfers measurement data from the measurement terminal 100 and an unillustrated measurement terminal to the health, management apparatus 300. The user terminal 200 displays a sugoroku activated by the health management apparatus 300.

The health management apparatus 300 is a server used by, for example, a service provider. The health management apparatus 300 includes an activation section 313, an obtaining section 314, an assessment section 315, determination section 316, and an update section 317. The activation section 313 manages sugoroku information for executing the sugoroku, and activates the sugoroku. The sugoroku includes a plurality of squares linking a starting square with a finishing square. The sugoroku is configured in such a manner that the user's piece is advanced through the squares, from the starting square toward the finishing square. The obtaining section 314 obtains measurement data on the user's biological information measured by the measurement terminal 100. The assessment section 315 assesses an evaluation value of the measurement data based on the obtained measurement data. The determination section 316 determines the number of squares through which the piece is to be advanced in the sugoroku, based on the assessed evaluation value. The update section 317 updates the location information indicating the square at which the piece is located, based on the determined number of squares, and stores the updated location information.

As described above, the health management apparatus 300 obtains the measurement data on the user's biological information, and advances the user's piece in the sugoroku based on the obtained measurement data. This enhances the user's motivation to measure biological information.

When the piece is advanced in the sugoroku, the health management apparatus 300 updates and stores the location information of the piece. Upon obtaining the next item of measurement data, the health management apparatus 300 further updates and stores the location information. That is, the measurement data obtained from time to time is continuously used in the sugoroku. Thereby, even when the user forgets to make a measurement once (e.g., one day), it is possible to maintain the user's motivation for the subsequent measurements.

The health management apparatus 300 assesses an evaluation value, namely, a level of importance based on the measurement data. Based on the assessed evaluation value, the number of squares through which the piece is to be advanced in the sugoroku is determined. This facilitates a heightening of the user's motivation to measure biological information with a high level of importance. It is thereby possible to obtain measurement data with a high level of importance for the user, thus improving the quality of health management.

§ 2 Configuration Example

[Hardware Configuration]
<Measurement Terminal 100>

Figure 2:
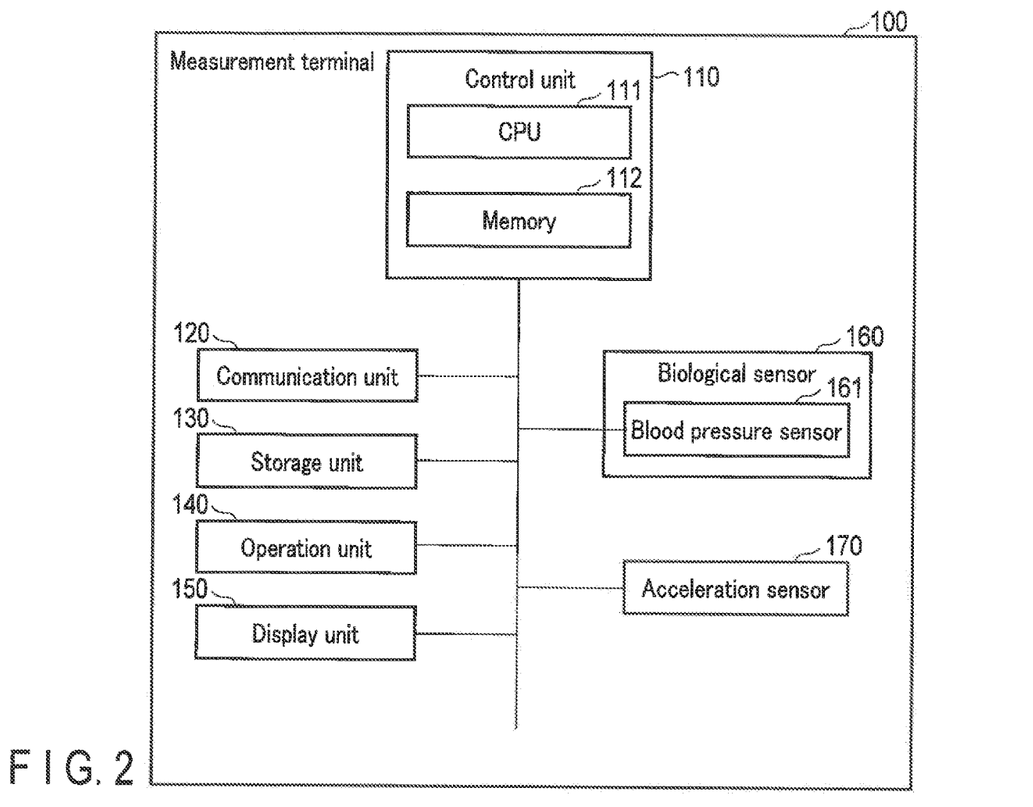
FIG. 2 schematically illustrates an example of a hardware configuration of a measurement terminal according to the embodiment.

Next, an example of a hardware configuration of the measurement terminal 100 according to the present embodiment will be described, with reference to FIG. 2. FIG. 2 schematically illustrates an example of a hardware configuration of the measurement terminal 100 according to the embodiment.

As shown in FIG. 2, the measurement terminal 100 according to the present embodiment includes a control unit 110, a communication unit 120, a storage unit 130, an operation unit 140, a display unit 150, a biological sensor 160, and an acceleration sensor 170.

The control unit 110 includes a central processing unit (CPU) 111 and a memory 112. The memory 112 includes a random access memory (RAM), a read-only memory (ROM), etc. The memory 112 stores programs executed by the CPU 111, and functions as a working memory. The control unit 110 performs various types of operation control, data processing, etc. when the CPU 111 executes the programs using the memory 112.

The communication unit 120 is a communication interface for communicating with the user terminal 200. The communication unit 120 transmits data to the user terminal 200 and receives data from the user terminal 200. Communication performed by the communication unit 120 may be either wireless or wired. In the present embodiment, let us assume that the communication unit 120 communicates with the user terminal 200 via short-range wireless communication. However, the communication unit 120 is not limited thereto, and may communicate using a communication cable or via a network such as a local area network (LAN).

The storage unit 130 stores, for example, a program for controlling the measurement terminal 100, setting data for setting various functions of the measurement terminal 100, measurement data measured by the biological sensor 160 and the acceleration sensor 170. The storage unit 130 may be used as a working memory when the program is executed.

The operation unit 140 includes operation devices such as a touch panel, operation buttons (operation keys), etc. The operation unit 140 detects an operation by the user and outputs an operation signal indicating the content of the operation to the control unit 110.

The display unit 150 includes a display screen (e.g., a liquid crystal display (LCD) or an electroluminescence (EL) display), an indicator, etc. The display unit 150 displays information according to a control signal from the control unit 110.

The biological sensor 160 measures the user's biological information. The biological sensor 160 includes, for example, a blood pressure sensor 161. The blood pressure sensor 161 measures the blood pressure as the user's biological information. The control unit 110 generates measurement data by associating the measured blood pressure with the time of day of measurement, the location of measurement, etc. The time of day of measurement is calculated based on time-of-day information provided by an unillustrated clock unit. The location of measurement is identified based on location information provided by an unillustrated location identification unit (e.g., the global positioning system (GPS)).

The blood pressure sensor 161 is, for example, a continuous-measurement blood pressure sensor. The continuous-measurement blood pressure sensor continuously measures the blood pressure (e.g., the systolic blood pressure and the diastolic blood pressure). The continuous-measurement blood pressure sensor continuously measures the blood pressure per beat, but is not limited thereto.

For the continuous-measurement blood pressure sensor, a continuous-measurement blood pressure sensor based on, for example, the PTT method, the tonometry method, the optical method, the radio wave method, the ultrasonic method, etc. can be adopted. The PTT method is a method of measuring a pulse transmit time (PTT) and estimating the blood pressure from the measured pulse transmit time. The tonometry method is a method of measuring the blood pressure using information detected by a pressure sensor, by bringing the pressure sensor into direct contact with a biological site, through which an artery, such as the radial artery at the wrist, passes. The optical method, the radio wave method, and the ultrasound method are methods of applying light, radio waves, and ultrasound waves, respectively, to blood vessels and measuring the blood pressure from their reflected waves.

The blood pressure sensor 161 may include a blood pressure sensor that cannot perform continuous measurements (hereinafter referred to as a "discontinuous blood pressure sensor"). A discontinuous blood pressure sensor measures the user's blood pressure using, for example, a cuff as a pressure sensor (oscillometric method). Discontinuous blood pressure sensors (in particular, oscillometric blood pressure sensors) tend to provide higher measurement precision than continuous blood pressure sensors. Thus, the blood pressure sensor 161 may be configured to activate a discontinuous blood pressure sensor in place of a continuous blood pressure sensor, triggered by satisfaction of a certain condition. This allows the blood pressure sensor 161 to measure the blood pressure with higher precision.

By including a sensor other than the blood pressure sensor 161, the biological sensor 160 can measure, as the biological information, the pulse wave, the pulsebeat, the electrical activity of the heart, the heartbeat, the body temperature, etc., as well as the blood pressure.

The acceleration sensor 170 measures the acceleration received by the main body of the measurement terminal 100. The acceleration sensor 170 measures, for example, three-axis or six-axis acceleration. The control unit 110 calculates the user's activity information from the measured acceleration. The control unit 110 checks the user's sleep state from the user's activity information.

In addition to the measurement terminal. 100 (first measurement terminal), an unillustrated measurement terminal (second measurement terminal) may be provided. The second measurement terminal measures, for example, biological information such as the user's body weight. The second measurement terminal generates measurement data by associating the measured body weight with the time of day of measurement, etc. The second measurement terminal is wirelessly connected to, for example, the user terminal 200, and the measurement data is transmitted to the user terminal 200. However, the measurement data of the second measurement terminal is not limited thereto, and may be manually entered by the user into the user terminal 200. Multiple unillustrated measurement terminals may be further provided so as to be, for example, wirelessly connected to the user terminal 200.

<User Terminal 200>

Figure 3:
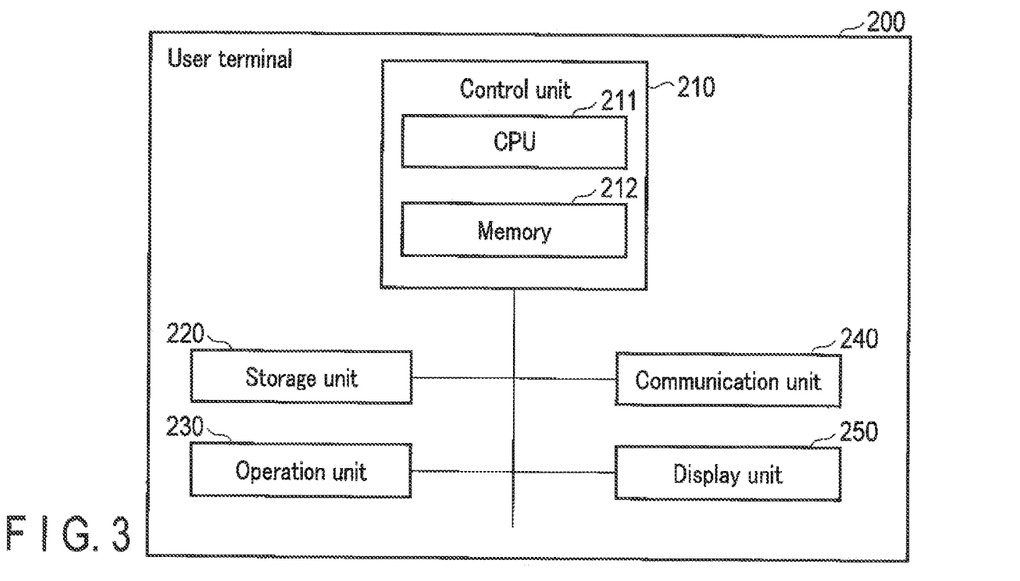
FIG. 3 schematically illustrates an example of a hardware configuration of a user terminal according to the embodiment.

Next, an example of a hardware configuration of the user terminal 200 according to the present embodiment will be described, with reference to FIG. 3. FIG. 3 schematically illustrates an example of a hardware configuration of the user terminal 200 according to the embodiment.

As shown in FIG. 3, the user terminal 200 according to the present embodiment includes a control unit 210, a storage unit 220, an operation unit 230, a communication unit 240, and a display unit 250.

The control unit 210 includes a CPU 211 and a memory 212. The memory 212 includes a RAM, a ROM, etc. The memory 212 stores a program to be executed by the CPU 211 and functions as a working memory. The control unit 210 performs various types of operation control, data processing, etc. by causing the CPU 211 to execute a program using the memory 212.

The storage unit 220 is an auxiliary storage device such as a hard disk drive, a solid state drive, etc. and stores a program to be executed by the control unit 210. The storage unit. 220 may store measurement data, etc. generated by the measurement terminal 100. The storage unit 220 may store display data, etc. displayed on the display unit 250.

The operation unit 230 includes, for example, a touch panel provided on the display screen of the display unit 250. The operation unit 230 is not limited thereto, and may include operation buttons, a keyboard, a mouse, etc. The operation unit 230 detects an operation made by the user, and outputs an operation signal indicating the content of the operation to the control unit 210, The measurement data may be manually entered via the operation unit 230.

The communication unit 240 is a communication interface for communicating with the measurement terminal 100 and the health management apparatus 300. The communication unit 240 transmits data to the measurement terminal 100 and receives data from the measurement terminal 100, The communication unit 240 transmits data to the health management apparatus 300 via the network 400 and receives data from the health management apparatus 300. Communication performed by the communication unit 240 may be either wireless or wired. In the present embodiment, let us assume that the network is, as an example, the Internet; however, the network is not limited thereto, and may be another type of network such as a LAN, or a one-to-one communication using a communication cable such as a USB cable.

The display unit 250 includes a display screen (e.g., an LCD or EL display). The display unit 250 displays information according to a control signal from the control unit 210. The display unit 250 displays the sugoroku activated by the health management apparatus 300.

<Health Management Apparatus 300>

Figure 4:
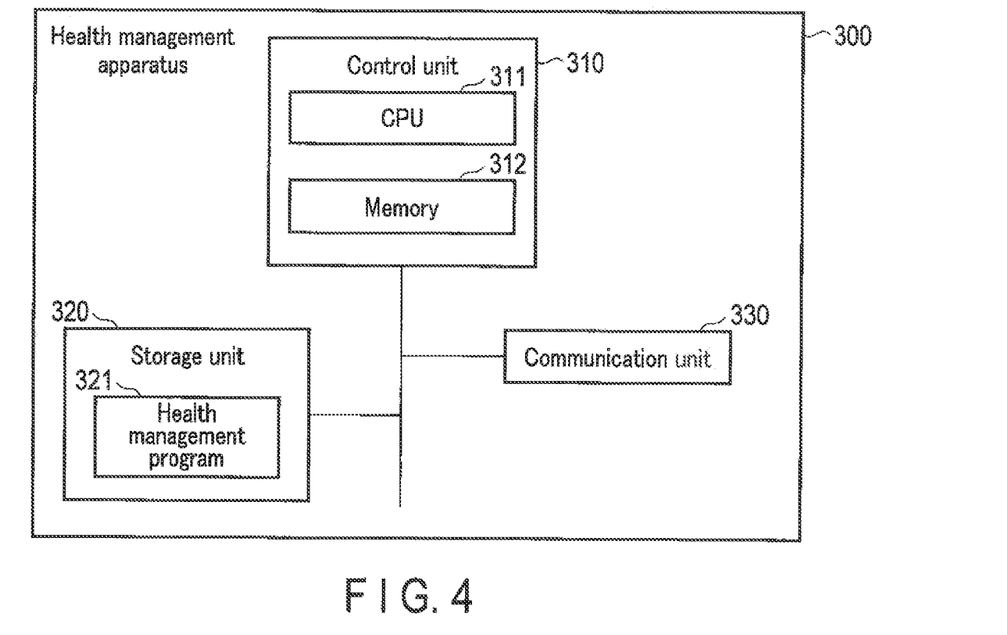
FIG. 4 schematically illustrates an example of a hardware configuration of the health management apparatus according to the embodiment.

Next, an example of a hardware configuration of the health management apparatus 300 according to the present embodiment will be described, with reference to FIG. 4. FIG. 4 schematically illustrates an example of a hardware configuration of the health management apparatus 300 according to the embodiment.

As shown in FIG. 4, the health management apparatus 300 according to the present embodiment includes a control unit 310, a storage unit 320, and a communication unit 330.

The control unit 310 includes a CPU 311 and a memory 312. The memory 312 includes a RAM, a ROM, etc. The memory 312 stores a program to be executed by the CPU 311, and functions as a working memory. The control unit 310 performs various types of operation control, data processing, etc. when the CPU 311 executes the program using the memory 312.

The storage unit 320 is an auxiliary storage device such as a hard disk drive, a solid state drive, etc. and stores a health management program 321 to be executed by the control unit 310.

The communication unit 330 is a communication interface for communicating with the user terminal 200. The communication unit 330 transmits data to the user terminal 200 and receives data from the user terminal 200, via the network 400. Communication performed by the communication unit 330 may be either wireless or wired.

[Functional Configuration]

<Health Management Apparatus 300>

Figure 5:
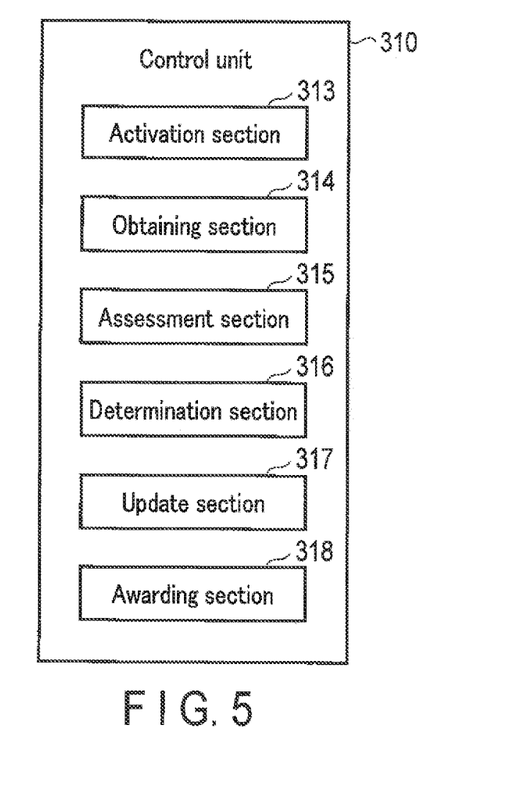
FIG. 5 schematically illustrates an example of a functional configuration of the control unit in the health management apparatus according to the embodiment.

Next, an example of a functional configuration of the control unit 310 in the health management apparatus 300 according to the present embodiment will be described, with reference to FIG. 5. FIG. 5 schematically illustrates an example of a functional configuration of the control unit 310 in the health management apparatus 300 according to the embodiment.

The control unit 310 of the health management apparatus 300 loads the health management program 321 stored to the storage unit 320 in the memory 312. The control unit 310 causes the CPU 311 (processor) to interpret and execute the health management program 321 loaded to the memory 312, and controls components. Thereby, the control unit 310 of the health management apparatus 300 according to the present embodiment functions as a computer including the activation section 313, the obtaining section 314, the assessment section 315, the determination section 316, the update section 317, and an awarding section 318, as shown in FIG. 5.

The activation section 313 manages sugoroku information for executing the sugoroku, and activates the sugoroku.

Figure 6:
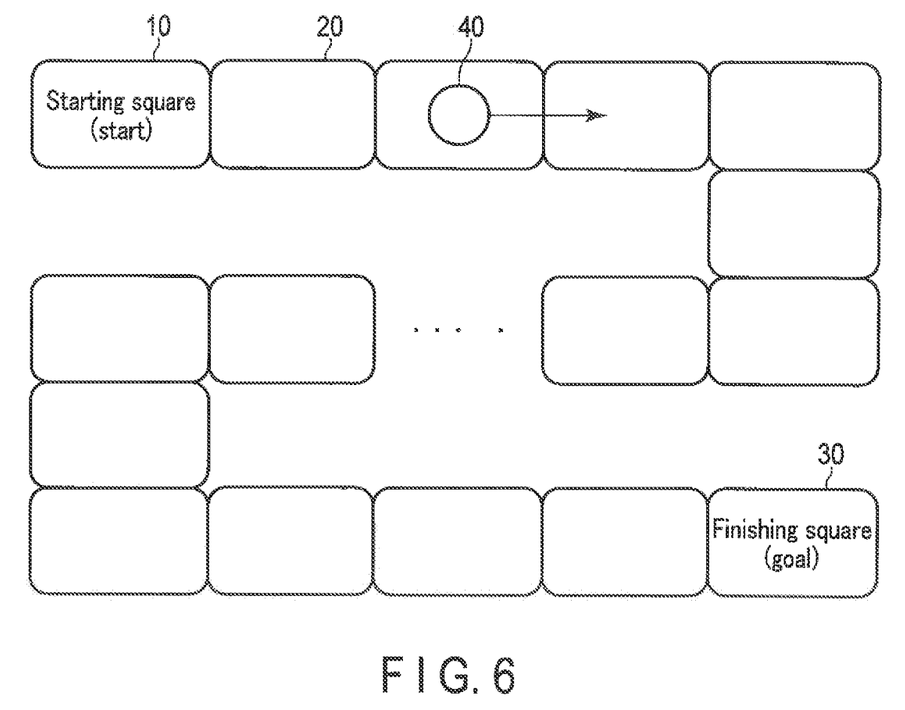
FIG. 6 schematically illustrates an example of a sugoroku activated by an activation section according to the embodiment.

FIG. 6 schematically illustrates an example of a sugoroku to be activated by the activation section 313 according to the embodiment.

As shown in FIG. 6, the sugoroku includes a starting square (start) 10 and a finishing square (goal) 30. The sugoroku includes a plurality of squares 20, linking the starting square 10 with the finishing square 30. The sugoroku is configured to direct the user's piece 40 through the squares 20, from the starting square 10 toward the finishing square 30. The finishing square 30 of the sugoroku may be associated with the user's target value.

Referring back, as shown in FIG. 5, the obtaining section 314 obtains measurement data on the user's biological information measured by either the measurement terminal 100 or an unillustrated measurement terminal. The measurement data contains the measured biological information and information on the time of day of measurement, the location of measurement, etc. Let us assume, as an example, that the biological information is the blood pressure or the body weight. However, the biological information is not limited thereto, and the pulse wave, the pulsebeat, the electrical activity of the heart, the heartbeat, the body temperature, etc. may be used instead.

The obtaining section 314 determines whether or not the obtained measurement data is the first item of data in the same period of time on the same day. If the obtained measurement data is the first item of data in the same period of time on the same day, the obtaining section 314 regards the measurement data as valid. On the other hand, if the obtained measurement data is not the first item of data in the same period of time on the same day, the obtaining section 314 regards the measurement data as invalid. That is, in this example, only the first item of measurement data in the same period of time on the same day is regarded as valid, and the second and subsequent items of measurement data are regarded as invalid. In this example, one day is divided into, for example, separate periods of time, including morning (e.g., from 04:00 to 11:45), evening (e.g., from 19:00 to 01:59), and night (e.g., from 02:00 to 03:59). The night may indicate a period over which the user is sleeping, and the sleep may be recognized with the measurement terminal 100.

The assessment section 315 assesses an evaluation value of the measurement data based on the obtained measurement data. More specifically, the assessment section 315 obtains the user's health information. Subsequently, the assessment section 315 checks the user's health information, and identifies a predetermined condition based on the checked health information. Thereafter, the assessment section 315 determines whether or not the measurement data satisfies the identified predetermined condition. The assessment section 315 assesses the evaluation value as a first value if the measurement data does not satisfy the predetermined condition. On the other hand, the assessment section. 315 determines that the evaluation value is a second value that is higher in evaluation than the first value if the measurement data satisfies the predetermined condition. The number of the evaluation values is not limited to two (the first value and the second value), and may be three or more.

The evaluation value of the measurement data is a value indicating the level of importance of the measurement data to the user. The user's health information is information indicating the user's health state, such as the result of diagnosis conducted by a medical institution. The predetermined condition based on the health information (health state) is a condition set according to, for example, the onset factors (the onset time and the onset place) of the health state.

Figure 7:
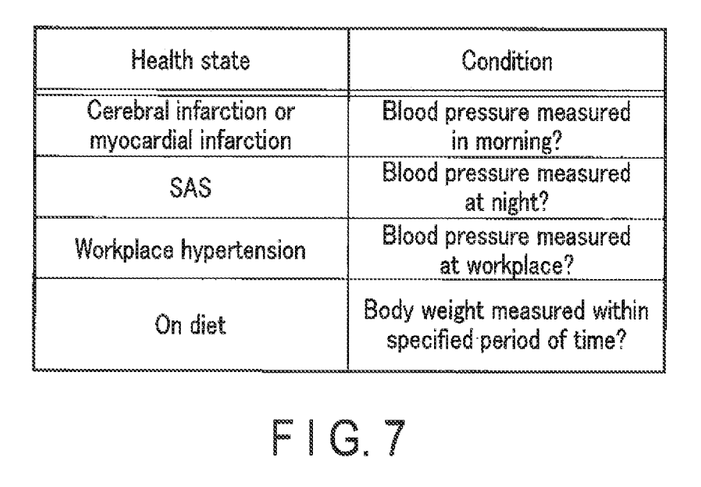
FIG. 7 illustrates an example of correspondence relationships between health states and predetermined conditions according to the embodiment.

FIG. 7 illustrates an example of correspondence relationships between health states and predetermined conditions according to the embodiment. That is, the assessment section 315 refers to these correspondence relationships and determines whether or not the measurement data satisfies the predetermined condition based on the health information. This correspondence table is stored in the storage unit 320. As described above, the measurement data contains the biological information (the blood pressure, the body weight, etc.), information on the time of day of measurement, and the location of measurement.

The onset of cerebral infarction and myocardial infarction is likely to occur in the morning, as shown in FIG. 7. Accordingly, the information on the blood pressure measured in the morning is important for users with cerebral infarction or myocardial infarction. Thus, if the users health state is one of cerebral infarction or myocardial infarction, the assessment section 315 determines whether or not the measurement data is information on the blood pressure measured in the morning. If the measurement data is determined as information on the blood pressure measured in the morning, the assessment section 315 assesses the evaluation value as high.

The onset of sleep apnea syndrome (SAS) occurs at night. Accordingly, the information on the blood pressure measured at night is important for users with sleep apnea syndrome. Thus, if the user's health state is one of sleep apnea syndrome, the assessment section 315 determines whether or not the measurement data is information on the blood pressure measured at night. If the measurement data is determined as information on the blood pressure measured at night, the assessment section 315 assesses the evaluation value as high.

In the case of sleep apnea syndrome, it is important to measure a rapid change in blood pressure (blood pressure surge) caused by apnea at night. Thus, it is desirable to continuously measure the blood pressure at night.

The onset of workplace hypertension occurs at the workplace. Accordingly, the information on the blood pressure measured at the workplace is important for users with workplace hypertension. Therefore, when the health state of the user is one of workplace hypertension, the assessment section 315 determines whether or not the measurement data is information on the blood pressure measured at the workplace. If the measurement data is determined as information on the blood pressure measured at the workplace, the assessment section 315 assesses the evaluation value as high.

The body weight varies during the day. Accordingly, the information on the body weight measured within a specified period of time, namely, within the same period of time (e.g., the morning or evening) is important for users who are going on a diet. Therefore, if the user is going on a diet, the assessment section 315 determines whether or not the measurement data is information on the body weight measured within a specified period of time. If the measurement data is determined as information on the body weight measured within the specified period of time, the assessment section 315 assesses the evaluation value as high.

Also, the information on the body weight measured over multiple periods of time (e.g., the morning and evening) is important for users who are going on a diet. Therefore, if the user is going on a diet and the body weight has been measured over multiple periods of time, the assessment section 315 may assess the evaluation value as high. For example, the assessment section 315 may assess the evaluation value as high if the evening measurement data is obtained when the morning measurement data has already been obtained.

The health state and the predetermined condition are not limited to the above-described ones, and other health conditions and other predetermined conditions may be suitably set.

Referring back, as shown in FIG. 5, the determination section 316 determines the number of squares through which the piece 40 is to be advanced in the sugoroku, based on the assessed evaluation value. More specifically, if the assessed evaluation value is low (a first value), the determination section 316 determines the number of squares through which the piece 40 is to be advanced as a first number (e.g., one). On the other hand, if the assessed evaluation value is high (a second value), the determination section 316 determines the number of squares through which the piece 40 is to be advanced as a second number (e.g., two) greater than the first number.

The number of squares through which the piece 40 is to be advanced is not limited to two (the first number and the second number), and may be three or more. Various events may occur in each square 20.

The update section 317 updates the location information of the piece 40 based on the determined number of squares. The location information indicates the square 20 at which the piece 40 is located. The update section. 317 stores the updated location information. The update section 317 determines whether or not the piece 40 has been advanced to the finishing square 30 (whether or not the square 20 indicated by the updated location information has become the finishing square 30).

The awarding section 318 awards a point to the user if the square 20 indicated by the location information has become the finishing square 30, namely, if the piece 40 has reached the goal. The point(s) may be exchanged for a predetermined prize. The awarding section 318 may be configured to issue, for example, a coupon to the user, instead of awarding a point.

Part of the functions (processes) realized by the health management apparatus 300 may be executed by the user terminal 200.

§ 3 Example of Operation

[Health Management Apparatus 300]

Figure 8:
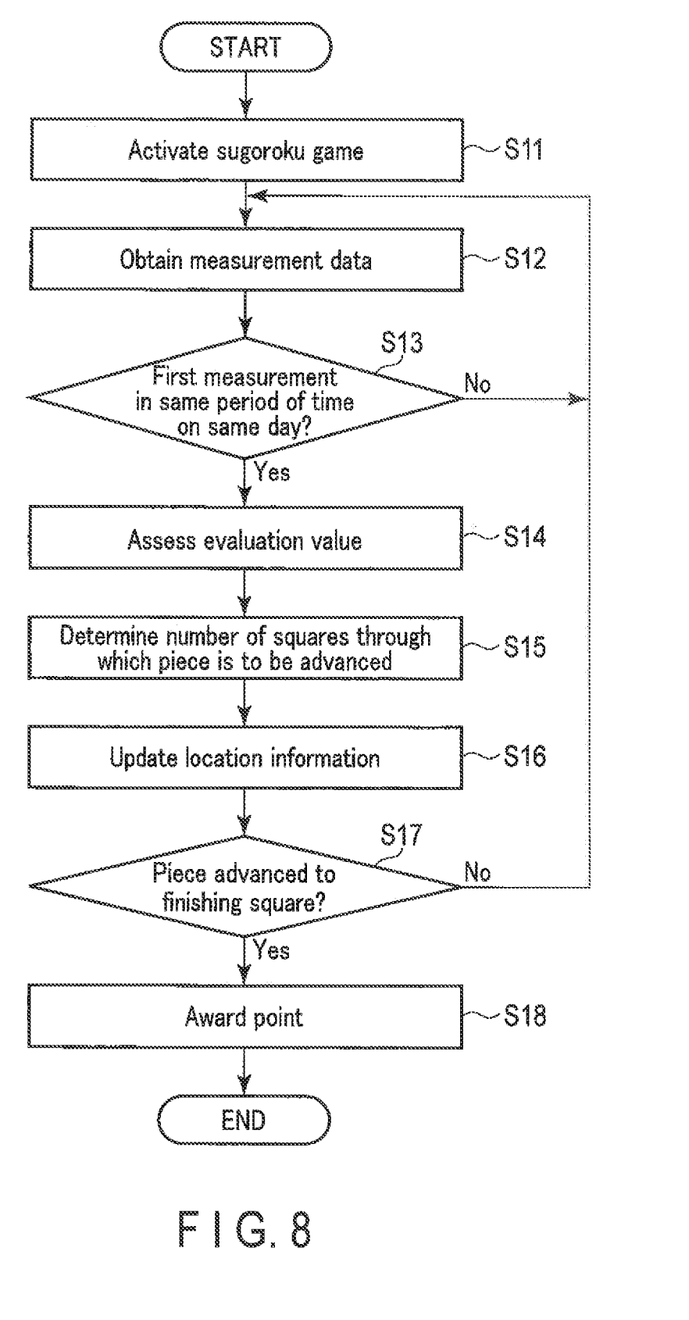
FIG. 8 is a flowchart: illustrating an example of a processing procedure of the health management apparatus according to the embodiment.

Next, an operation example of the health management apparatus 300 according to the present embodiment will be described, with reference to FIG. 8. FIG. 8 is a flowchart illustrating an example of a processing procedure of the health management apparatus 300 according to the embodiment. The processing procedure that will be described below is merely an example, and the processes may be changed where possible. In the processing procedure described below, steps may be appropriately omitted, substituted, and added, according to the embodiment.

(Step S11)

In step 311, the control unit 310 functions as the activation section 313 and activates the sugoroku.

(Step S12)

In the next step S12, the control unit 310 functions as the obtaining section 314, and obtains measurement data on the user's biological information measured by the measurement terminal 100 or a measurement terminal other than the measurement terminal 100.

(Step S13)

In the next step S13, the control unit 310 functions as the obtaining section 314. In step S13, the control unit 310 determines whether or not the measurement data obtained in step 312 is the first item of data in the same period of time on the same day. If the measurement data is determined in step S13 as the first item of data in the same period of time on the same day, the processing proceeds to step S14. On the other hand, if the measurement data is determined in step S13 as not being the first item of data in the same period of time on the same day (in the case of the second and subsequent items of data), the processing returns to step S12. That is, in step S12, the control unit 310 obtains the next item of measurement data.

In this example, one day is divided into, for example, separate periods of time, including morning, evening, and night. That is, in this example, only one item of measurement data is regarded as valid in each of the morning, the evening, and the night. For example, even when the user performs measurements twice in the morning, the measurement data obtained by the second and subsequent measurements in the morning becomes invalid.

(Step S14)

In the next step S14, the control unit 310 functions as the obtaining section 314. If the measurement data is the first item of data in the same period of time on the same day in step S13, the control unit 310 assesses the evaluation value of the measurement data based on the measurement data in step S14.

(Step S15)

In the next step S15, the control unit 310 functions as the determination section 316, and determines the number of squares through which the piece 40 is to be advanced based on the evaluation value determined in step S13.

(Step S16)

In the next step S16, the control unit 310 functions as the update section 317, and updates the location information of the piece 40 based on the number of squares determined in step S15.

(Step S17)

In the next step S17, the control unit 310 functions as the update section 317, and determines whether or not the piece 40 has been advanced to the finishing square 30 (whether or not the square 20 indicated by the location information has become the finishing square 30). If the piece 40 has been advanced to the finishing square 30 in step S17, the processing proceeds to step S18. On the other hand, if the piece 40 has not been advanced to the finishing square 30 in step 317, the processing returns to step S12. That is, in step S12, the control unit 310 obtains the next item of measurement data.

(Step S18)

In the next step S18, the control unit 310 functions as the awarding section 318. If the piece 40 has been advanced to the finishing square 30 in step S17, the control unit 310 awards a point to the user in step S18.

In this manner, the processing of the health management apparatus 300 according to the present embodiment is finished.

Figure 9:
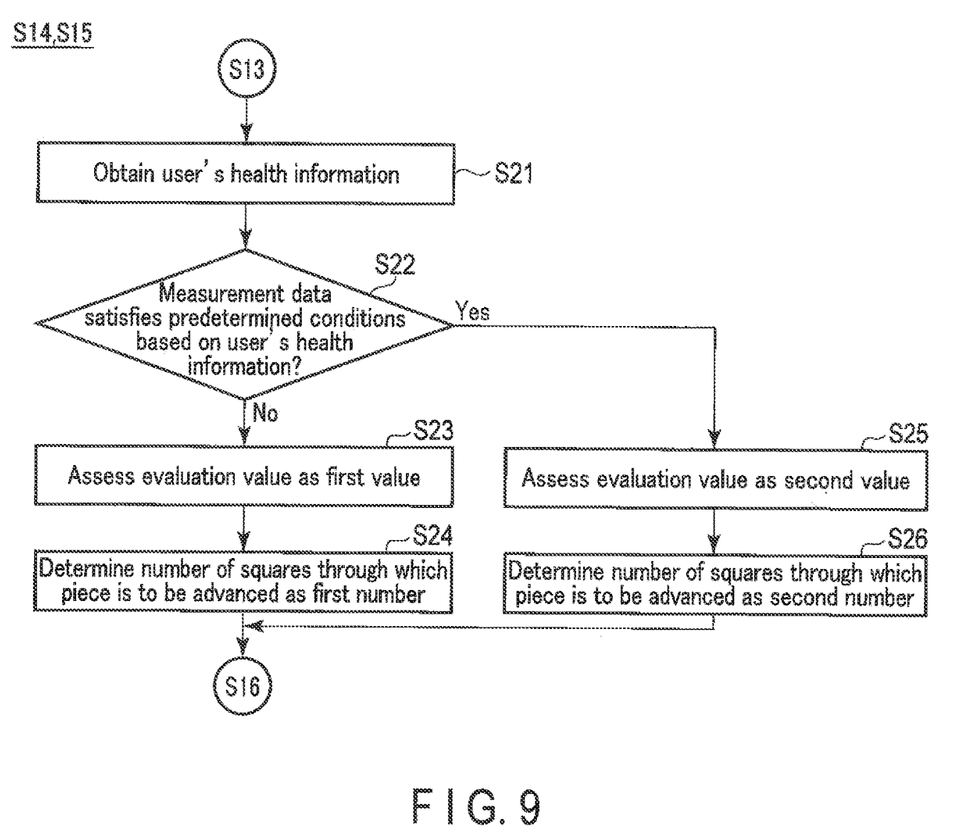
FIG. 9 is a flowchart illustrating an example of a processing procedure of the health management apparatus according to the embodiment.

Next, steps S14 and S15 in FIG. 8 will be described in more detail with reference to FIG. 9. FIG. 9 is a flowchart illustrating an example of a processing procedure performed by the health management apparatus 300 according to the embodiment, showing, in more detail, steps S14 and S15 (the evaluation value assessment process and the number-of-squares determination process) of FIG. 8.

(Step S21)

In step S21 following step S13, the control unit 310 functions as the assessment section 315, and obtains health information indicating the user's health state.

(Step S22)

In the next step S22, the control unit 310 functions as the assessment section 315, and determines whether or not the measurement data satisfies a predetermined Condition based on the user's health information. If the measurement data does not satisfy the predetermined condition based on the user's health information in step S22, the processing proceeds to step S23. On the other hand, if the measurement data satisfies the predetermined condition based on the user's health information in step S23, the processing proceeds to step S25.

(Step S23)

In step S23, the control unit 310 functions as the assessment section 315. If the measurement data does not satisfy the predetermined condition based on the user's health information in step S22, the control unit 310 assesses the evaluation value as a first value in step S23.

(Step S24)

In the next step S24, the control unit 310 functions as the determination section 316. In step S24, the control unit 310 determines the number of squares through which the piece 40 is to be advanced as a first number, based-on the evaluation value assessed as the first value in step S23.

(Step S25)

In step S25, the control unit 310 functions as the assessment section 315. If the measurement data satisfies the predetermined condition based on the user's health information in step S22, the control unit 310 assesses the evaluation value as a second value, which is higher in evaluation than the first value, in step S25.

(Step S26)

In the next step S26, the control unit 310 functions as the determination section 316. In step S26, the control unit 310 determines the number of squares through which the piece 40 is to be advanced as a second number, which is greater than the first number, based on the evaluation value assessed as the second value in step S25.

In this manner, the evaluation value assessment process and the number-of-squares determination process are completed, and the processing proceeds to step S16.

§ 4 Functions and Effects

In the present embodiment, the health management apparatus 300 activates a sugoroku for the user, as described above. The health management apparatus 300 obtains measurement data on the user's biological information, and advances the user's piece 40 in the sugoroku based on the obtained measurement data. This enhances the user's motivation to measure biological information.

When the piece 40 is advanced in the sugoroku, the health management apparatus 300 updates and stores the location information of the piece 40. Upon obtaining the next item of measurement data, the health management apparatus 300 further updates and stores the location information. That is, the measurement data obtained from time to time is continuously used in the sugoroku. Thereby, even when the user forgets to make a measurement once (e.g., one day), it is possible to maintain the user's motivation for the subsequent measurements.

The health management apparatus 300 assesses an evaluation value, namely, a level of importance based on the measurement data and the user's health information. Based on the assessed evaluation value, the number of squares through which the piece 40 is to be advanced in the sugoroku is determined. For example, if the evaluation value is high, the number of squares through which the piece 40 is to be advanced is large. This facilitates a heightening of the user's motivation to measure biological information with a high level of importance. It is thereby possible to obtain measurement data with a high level of importance for the user, thus improving the quality of health management.

The present invention is not limited to the above-described embodiment, and may be embodied in practice by modifying the structural elements without departing from the gist of the invention. In addition, various inventions can be made by suitably combining the components disclosed in connection with the above-described embodiments. For example, some of the components described in the embodiments may be deleted. Moreover, components described in different embodiments may be suitably combined.

What is claimed is:

1. A health management apparatus comprising:
a communication unit that communicates with a terminal external to the health management apparatus to transmit and receive data to and from the terminal;
a processor configured to:
generate a sugoroku including a plurality of squares linking a starting square with a finishing square, and configured to direct a piece of a user to be advanced through the squares from the starting square toward the finishing square;
obtain measurement data from the terminal via a wide-area network using the communication unit, the measurement data including biological information of the user and a time of day of measurement or a location of measurement at which the biological information has been measured;
assess an evaluation value based on whether or not the time of day of measurement or the location of measurement of the obtained measurement data satisfies a predetermined condition;
determine a number of squares through which the piece is to be advanced in the sugoroku, based on the assessed evaluation value; and
update location information indicating a square at which the piece is located, based on the determined number of squares.

2. The health management apparatus according to claim 1, wherein the processor is further configured to award a point to the user when the square indicated by the location information has become the finishing square.

3. The health management apparatus according to claim 1, wherein the processor is further configured to obtain health information indicating a health state of the user, and assesses the evaluation value based on the obtained measurement data and the health information.

4. The health management apparatus according to claim 3, wherein the processor is further configured to assess the evaluation value as a first value when the obtained measurement data does not satisfy a predetermined condition that is based on the obtained health information, and assesses the evaluation value as a second value higher in evaluation than the first value when the obtained measurement data satisfies the predetermined condition that is based on the obtained health information.

5. The health management apparatus according to claim 4, wherein the processor is further configured to determine the number of squares through which the piece is to be advanced as a first number when the evaluation value is determined as the first value, and determines the number of squares through which the piece is to be advanced as a second number greater than the first number when the evaluation value is determined as the second value.

6. The health management apparatus according to claim 1, wherein the measurement data includes a blood pressure and the time of day of measurement.

7. The health management apparatus according to claim 1, wherein the measurement data includes a blood pressure and the location of measurement.

8. The health management apparatus according to claim 1, wherein the measurement data includes a body weight and the time of day of measurement.

9. A health management method for execution by an apparatus that manages a health state of a user and includes a communication unit that communicates with a terminal external to the apparatus to transmit and receive data to and from the terminal, the method comprising:
- a step of generating a sugoroku including a plurality of squares linking a starting square with a finishing square, and configured to direct a piece of a user to be advanced through the squares from the starting square toward the finishing square;
- a step of obtaining measurement data from the terminal via a wide-area network using the communication unit, the measurement data including biological information of the user and a time of day of measurement or a location of measurement at which the biological information has been measured;
- a step of assessing an evaluation value based on whether or not the time of day of measurement or the location of measurement of the obtained measurement data satisfies a predetermined condition;
- a step of determining a number of squares through which the piece is to be advanced in the sugoroku, based on the assessed evaluation value; and
- a step of updating location information indicating a square at which the piece is located, based on the determined number of squares.

10. A non-transitory computer readable medium storing a health management program causing a processor to:
- generate a sugoroku including a plurality of squares linking a starting square with a finishing square, and configured to direct a piece of a user to be advanced through the squares from the starting square toward the finishing square;
- obtain measurement data from a terminal external to a processor via a wide-area network using a communication unit, the communication unit communicating with the terminal to transmit and receive data to and from the terminal, the measurement data including biological information of the user and a time of day of measurement or a location of measurement at which the biological information has been measured;
- assess an evaluation value based on whether or not the time of day of measurement or the location of measurement of the obtained measurement data satisfies a predetermined condition;
- determine a number of squares through which the piece is to be advanced in the sugoroku, based on the assessed evaluation value; and
- update location information indicating a square at which the piece is located, based on the determined number of squares.

\* \* \* \* \*